United States Patent
Burke

(10) Patent No.: US 11,819,221 B2
(45) Date of Patent: Nov. 21, 2023

(54) CUTTING ACCESSORY FOR A POWERED SURGICAL HANDPIECE

(71) Applicant: Stryker European Operations Holdings LLC, Kalamazoo, MI (US)

(72) Inventor: Thomas Gerald Burke, Claremorris (IE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 449 days.

(21) Appl. No.: 16/988,837

(22) Filed: Aug. 10, 2020

(65) Prior Publication Data

US 2020/0367911 A1 Nov. 26, 2020

Related U.S. Application Data

(60) Division of application No. 15/423,736, filed on Feb. 3, 2017, now Pat. No. 10,736,642, which is a
(Continued)

(51) Int. Cl.
*A61B 17/16* (2006.01)

(52) U.S. Cl.
CPC ........ *A61B 17/162* (2013.01); *A61B 17/1615* (2013.01); *A61B 17/1622* (2013.01); *A61B 17/1628* (2013.01); *A61B 17/1631* (2013.01)

(58) Field of Classification Search
CPC .. A61B 17/1631; A61B 17/162; B25D 17/08; B23B 2231/0256; B23B 2231/0268;
(Continued)

(56) References Cited

U.S. PATENT DOCUMENTS 3,507,508 A * 4/1970 Andrews ............. B23B 31/1075
 403/375
3,945,653 A * 3/1976 Falchle ................ B25D 17/088
 279/97
(Continued)

FOREIGN PATENT DOCUMENTS

DE 102012108266 A1 3/2014
JP 2014516611 A 7/2014
WO 2012138337 A1 10/2012

OTHER PUBLICATIONS

EPO, "ISA Search Report and Written Opinion for PCT App No. PCT/US2015/04222", dated Jan. 5, 2016.
(Continued)

*Primary Examiner* — David W Bates
(74) *Attorney, Agent, or Firm* — Howard & Howard Attorneys PLLC

(57) ABSTRACT

A cutting accessory for use with a powered surgical handpiece includes an elongated shaft, a tissue working member, and a proximal section. The elongated shaft has proximal and distal ends, and a longitudinal axis. The working member is attached to the distal end of the shaft. The proximal section extends proximally from the distal end and includes a plurality of faces extending inwardly from an outer surface of the shaft. Each face has at least one shallow portion and is shaped to receive a clamping member. At least two of the faces are arranged linearly, extending along the shaft proximal section. A flat extends distally forward of the distalmost face, and is located a distance from the shaft longitudinal axis greater than the distance the shallow portions are located from the longitudinal axis and less than the distance the outer surface of the shaft is from the longitudinal axis.

20 Claims, 15 Drawing Sheets

Related U.S. Application Data continuation of application No. PCT/US2015/042221, filed on Jul. 27, 2015.

(60) Provisional application No. 62/033,870, filed on Aug. 6, 2014.

(58) Field of Classification Search
CPC .... B23B 2231/0284; B23B 2231/0252; B23B 2231/0272
See application file for complete search history.

(56) References Cited

U.S. PATENT DOCUMENTS

| | | | |
|---|---|---|---|
| 4,234,201 A * | 11/1980 | Sorensen | B23B 31/103 279/131 |
| 4,255,145 A * | 3/1981 | Weissman | A61C 5/35 433/128 |
| 4,437,801 A * | 3/1984 | Lewis | B23B 31/10741 409/234 |
| 4,514,117 A * | 4/1985 | Scott | B23B 31/1075 408/239 R |
| 4,706,659 A * | 11/1987 | Matthews | B25G 1/025 464/57 |
| 4,850,758 A * | 7/1989 | Morgan | B23B 31/005 408/226 |
| 4,859,183 A * | 8/1989 | Martin | A61C 5/42 433/102 |
| 5,059,195 A | 10/1991 | Gray | |
| 5,403,134 A * | 4/1995 | Andersson | B23B 31/1076 408/239 R |
| 5,634,933 A * | 6/1997 | McCombs | B23B 31/107 408/226 |
| 5,660,400 A * | 8/1997 | Kasmeier | B23B 31/005 279/83 |
| 5,735,535 A | 4/1998 | McCombs et al. | |
| 5,888,200 A | 3/1999 | Walen | |
| 5,957,634 A * | 9/1999 | Carpinetti | B23B 51/126 279/143 |
| 6,126,521 A * | 10/2000 | Shearer | B21C 47/18 451/48 |
| 6,562,055 B2 | 5/2003 | Walen | |
| 7,422,582 B2 | 9/2008 | Malackowski et al. | |
| 7,559,927 B2 | 7/2009 | Shores et al. | |
| 8,597,316 B2 * | 12/2013 | McCombs | A61B 17/32002 606/167 |
| 10,092,302 B2 | 10/2018 | Overes et al. | |
| 10,736,642 B2 | 8/2020 | Burke | |
| 2002/0058958 A1 * | 5/2002 | Walen | A61B 17/32002 606/170 |
| 2003/0023256 A1 | 1/2003 | Estes et al. | |
| 2003/0055432 A1 | 3/2003 | Steiger | |
| 2003/0163134 A1 * | 8/2003 | Riedel | B23B 31/1072 606/167 |
| 2004/0081523 A1 * | 4/2004 | Vasudeva | B23B 31/005 408/240 |
| 2004/0194324 A1 | 10/2004 | Youn-Chyuan | |
| 2004/0253070 A1 * | 12/2004 | Sheffler | B23B 31/1075 409/234 |
| 2005/0238451 A1 * | 10/2005 | Hartman | B23B 31/1072 409/234 |
| 2005/0285355 A1 | 12/2005 | Lin | |
| 2007/0114730 A1 | 5/2007 | Duesing | |
| 2009/0325123 A1 | 12/2009 | Bailey et al. | |
| 2009/0326540 A1 | 12/2009 | Estes | |
| 2011/0008114 A1 * | 1/2011 | Wang | B23B 29/24 407/113 |
| 2012/0169002 A1 * | 7/2012 | Canuto | B23Q 3/103 269/296 |
| 2012/0253323 A1 | 10/2012 | Bharadwaj et al. | |
| 2013/0245629 A1 | 9/2013 | Xie | |
| 2013/0245704 A1 | 9/2013 | Koltz et al. | |
| 2014/0239599 A1 * | 8/2014 | Schweizer | B30B 15/026 279/66 |
| 2014/0324050 A1 | 10/2014 | Masson | |
| 2015/0238242 A1 | 8/2015 | Barth et al. | |
| 2015/0313612 A1 * | 11/2015 | Edwards | B23B 31/1071 606/80 |
| 2015/0327905 A1 * | 11/2015 | Barth | A61B 17/162 606/104 |
| 2019/0232388 A1 * | 8/2019 | Mori | B23B 51/06 |

OTHER PUBLICATIONS

English language abstract for JP 2014-516611 extracted from espacenet.com database on Dec. 2, 2020, 2 pages.

* cited by examiner

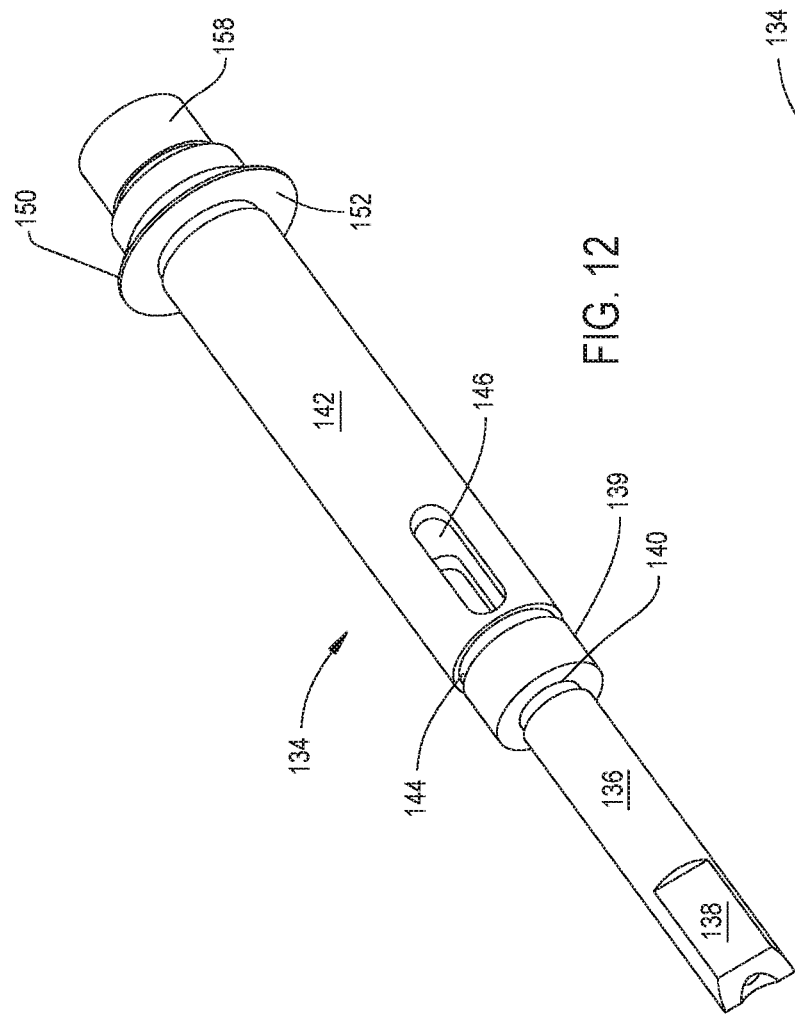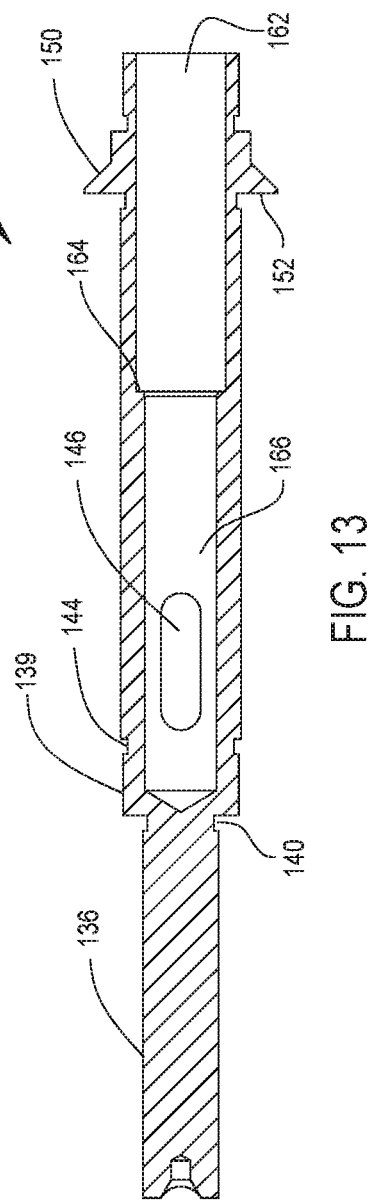
FIG. 12
FIG. 13

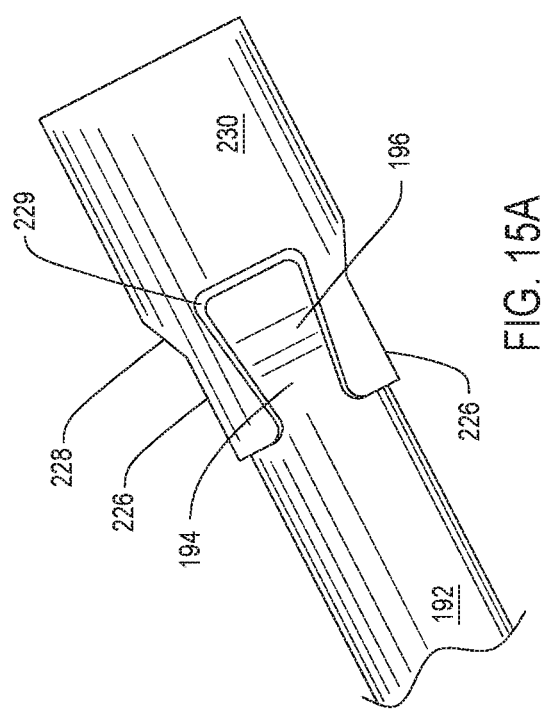
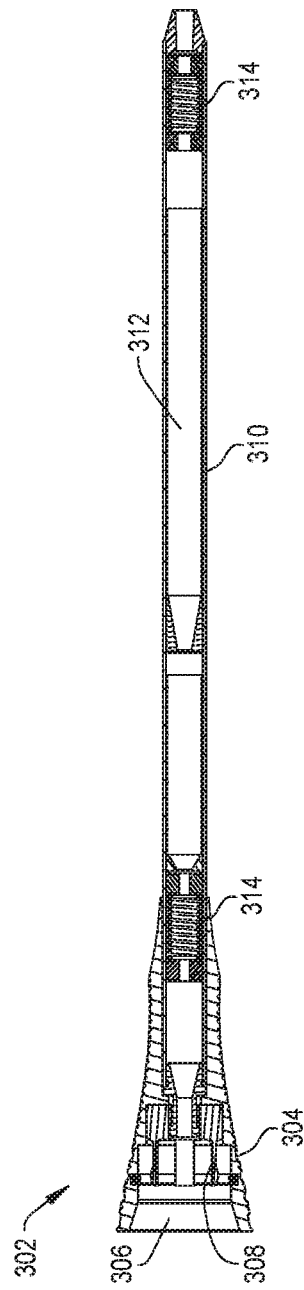

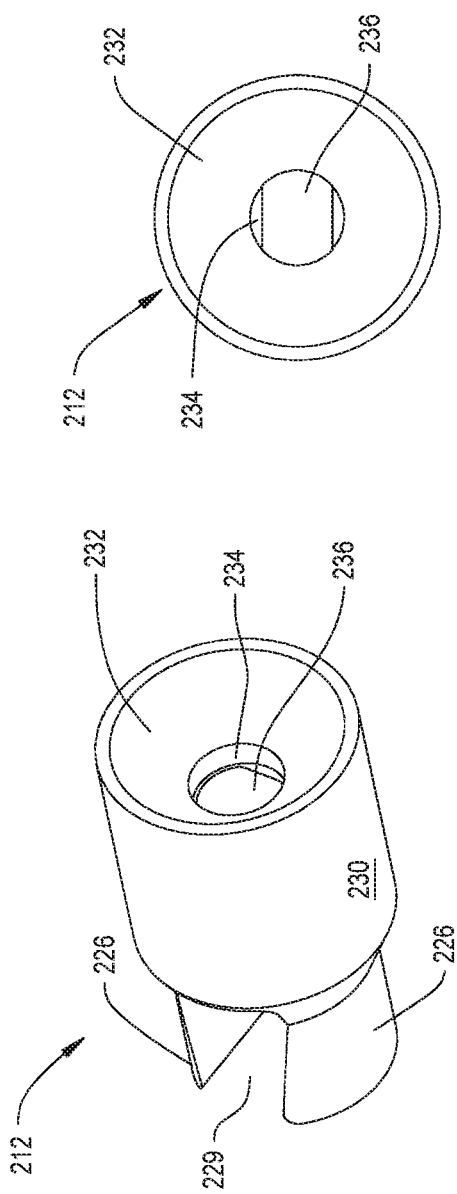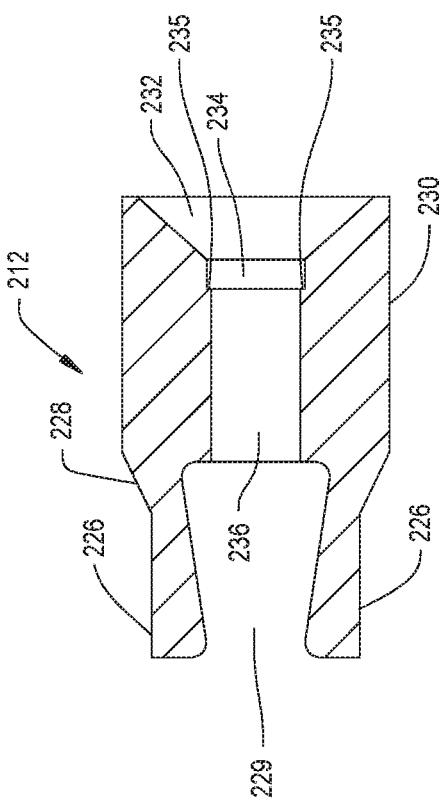
FIG. 16
FIG. 17
FIG. 18

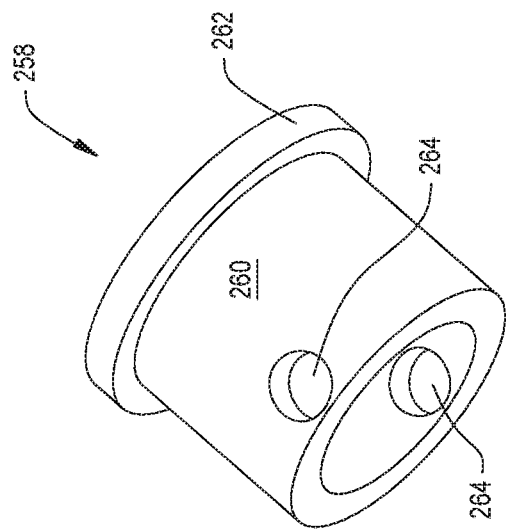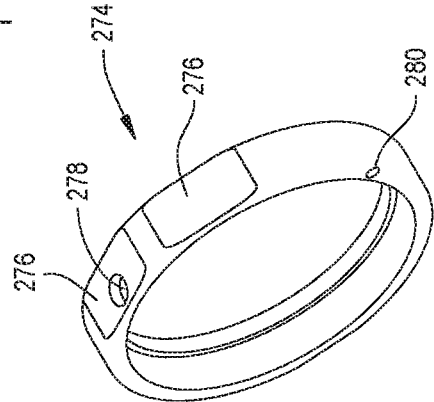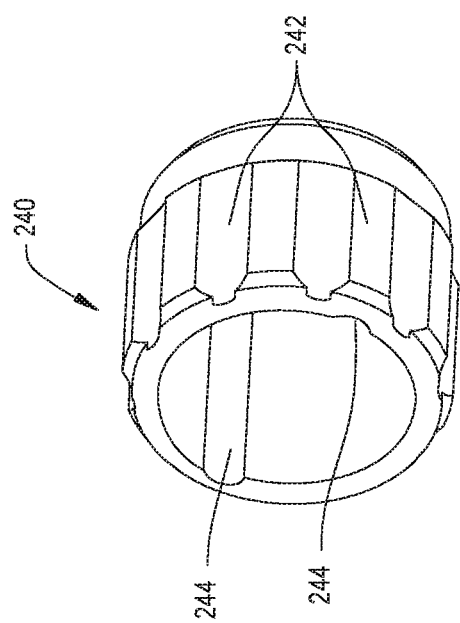

CUTTING ACCESSORY FOR A POWERED SURGICAL HANDPIECE

FIELD OF THE INVENTION

The present invention relates generally to a surgical tool system to which cutting accessories are selectively attached. More particularly, this invention relates to a surgical tool system with a cutting accessory that is configured to facilitate the alignment of the accessory with the chuck that holds the accessory to the tool handpiece.

BACKGROUND OF THE INVENTION

In modern surgery, one of the most important Instruments available to medical personnel is the powered surgical tool. Typically, this tool includes a handpiece in which a motor is housed. Secured to the handpiece is a cutting accessory. The cutting accessory is designed for application to a surgical site on a patient to accomplish a specific medical task. Some powered surgical tools are provided with drills or burs for cutting bores into hard tissue or for selectively removing the hard and soft tissue. Still other powered surgical tools are provided with saw blades as cutting accessories. These tools are used for separating large sections of hard and/or soft tissue. The ability to use powered surgical tools on a patient has lessened the physical strain of physicians and other medical personnel when performing procedures on a patient. Moreover, most surgical procedures can be performed more quickly, and more accurately, with powered surgical cools than with the manual equivalents that preceded them.

U.S. Pat. No. 5,888,200, entitled, MULTI-PURPOSE SURGICAL TOOL SYSTEM, issued 30 Mar. 1999, incorporated herein by reference, discloses a surgical tool system designed for a number of different applications. This tool system includes a handpiece in which a motor is housed. The handpiece also includes a first coupling assembly for selectively coupling the shaft of an accessory to the motor shaft. This handpiece also includes a second coupling assembly. The second coupling assembly is used to selectively secure an attachment to the front end of the handpiece. This attachment may include its own drive shaft and accessory coupling assembly. These attachments are elongated attachments, angled attachments and/or able to actuate saw blades. Thus, an advantage of providing this type of tool system is that a single handpiece can be used to drive a large number of different cutting accessories and facilitate the positioning of the accessories at the surgical site in a manner that is either required or desired for a particular surgical procedure.

A variation on this tool system is disclosed in U.S. Pat. No. 6,562,055, entitled CUTTING ATTACHMENT FOR A SURGICAL HANDPIECE DESIGNED TO BE SELECTIVELY COUPLED TO THE HANDPIECE, issued 13 May 2003 the contents of which is also explicitly incorporated herein by reference. This document discloses a surgical tool with a drive shaft that has an elongated bore. The drive shaft bore is sized to receive the proximal end of the shaft of the accessory. A collet is mounted to the drive shaft to rotate with the drive shaft. The collet has feet that project into the drive shaft bore. This assembly is further designed so that the accessory shaft can be selectively longitudinally positioned relative to the collet feet. This accessory is formed to have plural retention features disposed longitudinally along the length of the drive shaft. These features allows the practitioner to selectively set the extent to which the accessory shaft extends forward of the handpiece. Specifically, the practitioner may want to set the distal end of the accessory shaft, the end to which the tissue working member is attached, to extend a relatively short distance forward of the handpiece the shaft. The accessory is so set by positioning the accessory shaft so the distally located retention features are engaged by the collet feet. Alternatively, the practitioner can reposition the cutting accessory so that the tissue working member is located a relatively long distance away from the handpiece. To so configure the system, the shaft if longitudinally set relative to the collet so the proximally located retention features are the retention features against which the collet feet engage.

An advantage of the above construction is that a single cutting accessory can be positioned so that accessory head is located different distances from the handpiece. This eliminates the need to provide plural cutting accessories constructed so that the only distance between two different accessories is the overall length of the accessory shaft.

The above type of surgical tool system works well when the accessories have rigid shafts.

However, a number of different surgical tools system are provided with cutting accessories that have shafts that relatively thin and/or flexible. One type of surgical tool system provided with this type of thin flexible cutting accessory shaft is a minimally invasive surgical (MIS) tool system. An MIS tool system, as implied by its name, is designed to be applied to the surgical site in the patient through a relatively small opening, called a portal, formed in the patient. An objective behind performing an MIS procedure is to minimize the size of tee incision that is formed in the patient to access the site internal to the patient at which the procedure is to be performed. One reason this objective is desirable because it reduces the extent to which the patient's tissue needs to be returned to its original state and heal after surgery. Another advantage of performing an MIS procedure, as opposed to a procedure in which a larger incision is formed, is that the MIS procedure lessens the extent the tissue and organs internal to the body are exposed to the ambient environment. By extension, this reduces the extent to which the tissue of the patient is open to infection.

Many tools designed to perform an MIS procedure are relatively small in cross sectional width. This facilitates the fitting of the tool in the relatively small diameter portal formed in the patient. Some MIS tools are designed to be inserted into a circular opening that has a diameter of 2 cm or less. These tools themselves may have cross section diameter of 0.5 cm or less.

There are powered surgical tools, including cutting accessories, designed to be seated in these small diameter bores. Often this type of tool system has a front end attachment designed to be releasably attached to the handpiece. The cutting accessory is rotated by the handpiece motor and rotates within the attachment. Some of these attachments have longitudinal axes formed with a bend. The accessory shaft is flexible so the shaft bends the accessory is bent or angled.

For the accessory shaft to bend or flex or to fit within a small diameter attachment, the accessory shaft is typically designed to be relatively small in diameter. The flexible section of some accessory shafts have a diameter of 2 mm or less.

Problems arise owing to the small size and flexibility of these accessory shafts. These shafts can flex or rotate when inserted in handpiece. This flexure is generally away from the longitudinal axis through the shaft. The rotation is generally around the longitudinal axis. The flexure can occur during the process of inserting the accessory in the handpiece. When the flexure occurs, it may be necessary to rotate the shaft to place the shaft in a position in which the retention features are aligned with the complementary retention features integral with the chuck. Having to take this action can contribute to the overall time it takes to perform a surgical procedure. Adding the time to perform this task to the procedure goes against one of the objective of modern surgery. Specifically, it is goal of modern surgery to perform the procedure as quickly as possible to minimize the time the patient is held under anesthesia and the body of the patient is open and exposed to the ambient environment.

The undesirable rotation of the accessory shaft can occur during the procedure when the handpiece is actuated Specifically, when the handpiece is rotated, the whole of the accessory shaft is supposed to rotate at the same speed. However, owing to imposition of different forces on the different portions of the accessory and the flexible nature of the accessory shaft, there may some twist in the accessory shaft around the longitudinal axis of the shaft. As a result of this twist, and the natural tendency of the material forming the shaft to twist back to the untwisted state, the proximal end of the accessory shaft, the end of the shaft disposed in the drive shaft integral with the handpiece may want to rotate within the drive shaft. This rotation of the shaft can result in the shaft retention features rotating out of engagement with the collet feet or other chuck retention features that hold the shaft in position. If this type of accessory shaft-relative to-drive shaft movement occurs, the accessory shaft may not be firmly held in place to the drive shaft.

SUMMARY OF THE INVENTION

This invention relates to a new and useful surgical tool system. The surgical tool system of this invention includes a powered surgical handpiece and a cutting accessory that is rotated by the handpiece. The system of this invention includes a chuck with locking members integral with the handpiece. The system also includes retention features integral with the cutting accessory. The chuck locking members are designed to engage the accessory retention features so that, as a result of this engagement, the accessory rotates with the rotation of the locking members. The system of this invention is further designed so that the handpiece and cutting accessory have complementary features that, upon the fitting of the cutting accessory to the handpiece, align the accessory retention features with the chuck locking members. These features also inhibit the relative rotation of the accessory relative to the handpiece locking members.

In some constructions of the invention, the chuck includes an alignment collar. The alignment collar is located distally forward of the locking members. The alignment collar is formed with a non-circular opening. The accessory shaft is shaped so that at least the proximal section of the shaft is non-circular in shape. More particularly, the accessory shaft is shaped to closely slip fit in the opening in the alignment collar.

The alignment collar opening is in a specific orientation relative to the chuck locking elements. The retention features on the accessory shaft are in corresponding locations along the shaft.

As part of the process of readying a tool system of this invention for use, the accessory shaft is inserted in the chuck alignment collar. To so fit the accessory shaft, it is typically necessary to rotate the shaft so the non-circular portion of the shaft goes into registration with non-circular bore in the alignment collar. Once this alignment process is finished, it is easy matter to slide the shaft through the collar. Owing to the alignment of the accessory shaft with the chuck alignment collar the shaft retention features are aligned with the chuck locking elements.

The chuck alignment collar rotates with the rotation of the handpiece output shaft. Owing to the close fitting of the accessory shaft in the collar bore, the accessory shaft is forced by the collar into rotation with the collar. This inhibits the twisting of the relatively short length section of the accessory shaft located proximal to the collar. The elimination of this twisting results in a like elimination that the twisting would cause the accessory shaft to disengage from the chuck locking elements.

In some versions of the invention, the chuck includes a collet with spring like feet that function as the handpiece locking elements.

In some versions of the invention, the chuck is removably attached to the housing that contains the handpiece motor.

BRIEF DESCRIPTION OF THE DRAWINGS

The invention is pointed out with particularity in the claims. The above and further features and benefits of this invention are understood by the following Detailed Description taken in conjunction with the accompanying drawings. Unless otherwise stated, the relative dimensions of the components of as illustrated the drawings are generally understood to be the relative dimensions of the components to each other. In the accompanying drawings:

FIG. 11 is perspective view of the chuck spring ring;

FIG. 12 is a perspective view of the drive shaft internal to the chuck;

FIG. 13 is a cross sectional view of the drive shaft;

FIG. 15A depicts how the distal end of the collet is seated in the alignment collar;

FIG. 16 is a perspective view of the alignment collar;

FIG. 17 is a plan view of the distal end of the alignment collar;

FIG. 18 is a cross sectional view of the alignment collar;

FIG. 19 is a perspective view of the chuck lock collar;

FIG. 22 is a perspective view of the drive link internal to the chuck;

FIG. 23 is a perspective view of the torque ring internal to the chuck;

FIG. 24 is a cross sectional view of a nose of the surgical tool system;

DETAILED DESCRIPTION

Figure 1:
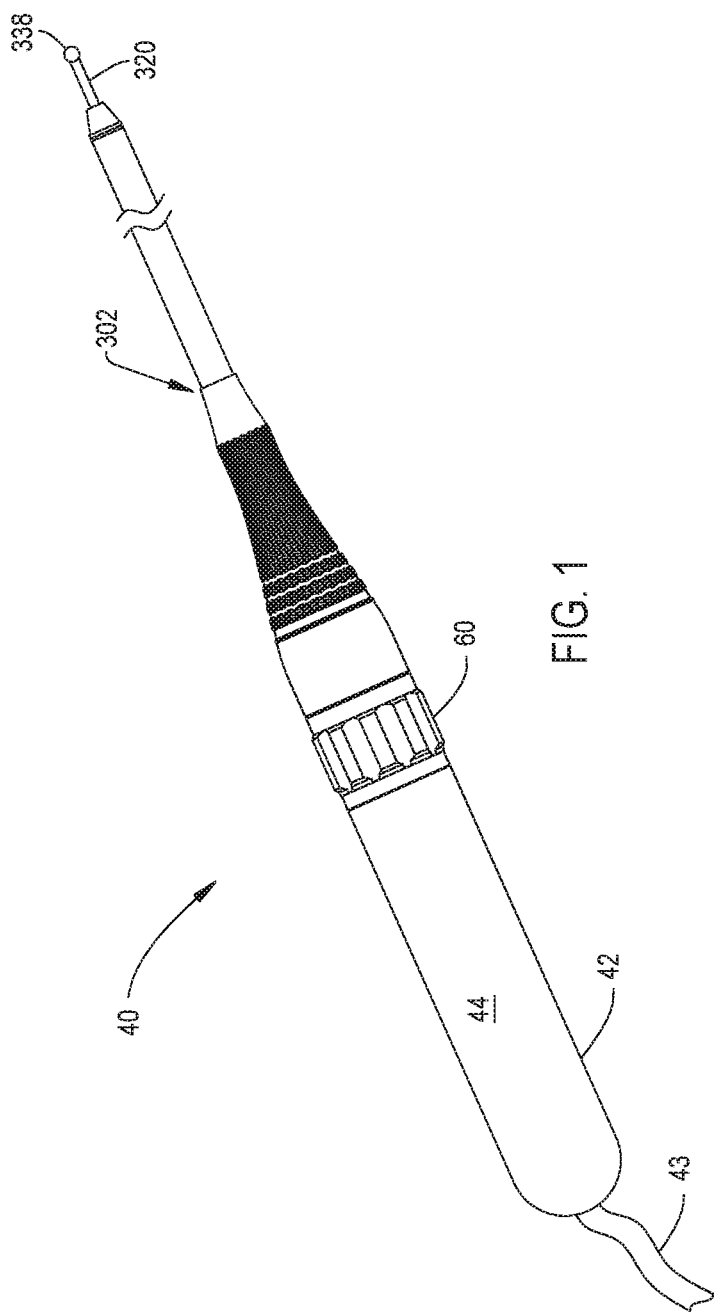
FIG. 1 is a plan view of a surgical tool system of this invention.
Figure 2:
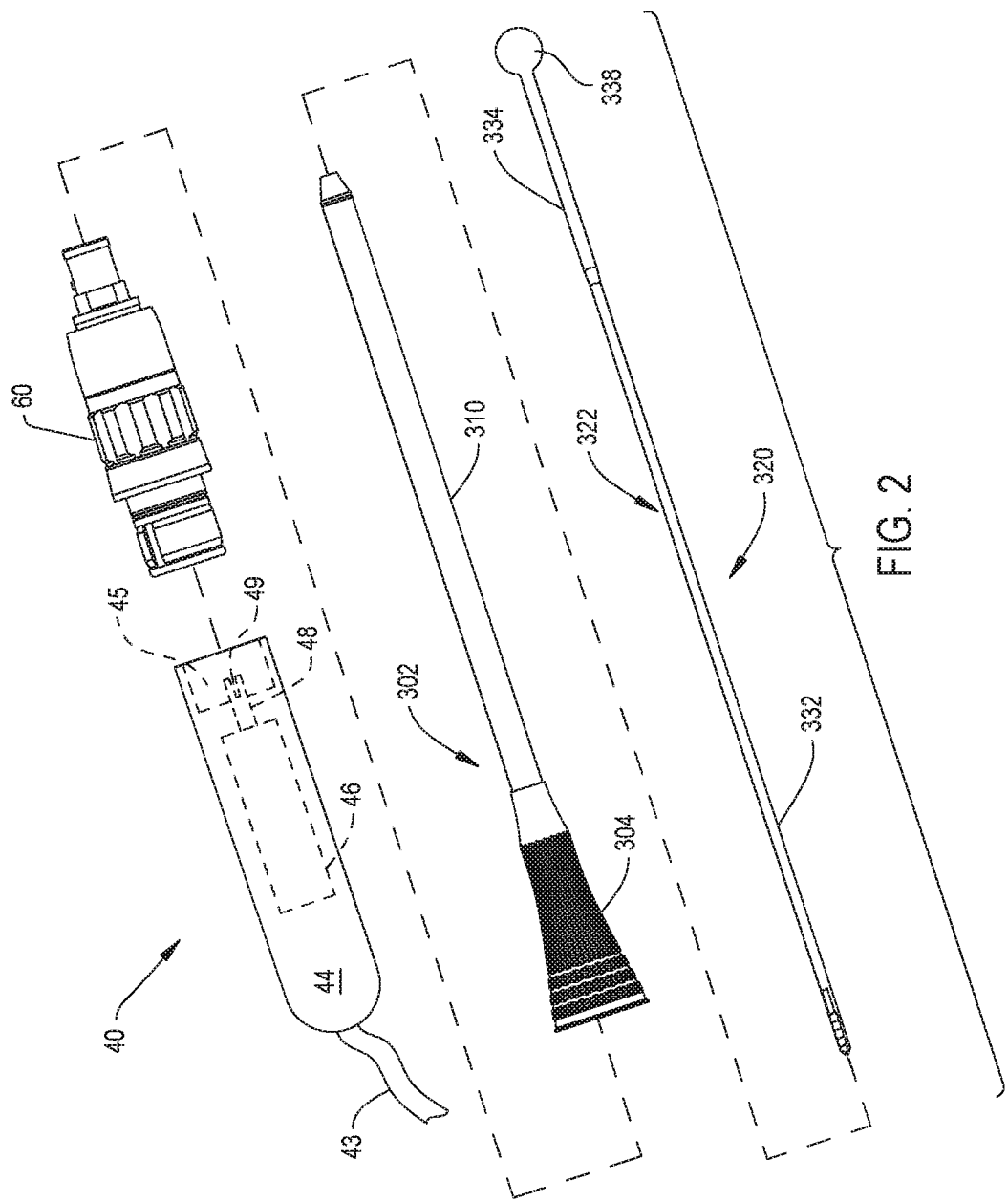
FIG. 2 is an exploded view of the basic components of the system of FIG. 1.

The basic components of a surgical tool system 40 of this invention are seen by reference to FIGS. 1 and 2. System 40 includes a handpiece 42. Handpiece 42 has a cylindrical body 44. Internal to handpiece body 44 is motor 46 that is represented as a phantom rectangle. Motor 46 rotates a drive spindle 48 represented by a second phantom rectangle. A chuck 60 is removably attached to the distal end of the handpiece body 44. ("Distal" is understood to mean away from the practitioner holding the handpiece 42, towards the surgical site at which a procedure is to be performed. "Proximal" is understood to mean towards the practitioner holding the handpiece 42, away from the surgical site at which the procedure is to be performed.) A nose 302 is removably attached to and extends forward from the distal end of chuck 60. A cutting accessory 320 is disposed inside the nose 302. Cutting accessory 320 is coupled to the chuck 60 and extends through and projects out the distal end of the nose 302. A tissue working member 338, which is located forward of nose 302, forms the distal end of the cutting accessory.

Internal to the chuck 60 is a drive shaft 134 (FIG. 12). The proximal end of the drive shaft is configured to engage and be rotated by the handpiece spindle 48. Components internal to the chuck 60 that are described below releasably hold the cutting accessory 320 to the drive shaft 134. The actuation of the motor 46 therefore results in the rotation of the cutting accessory 320.

Handpiece 42 is formed so that body 44 is generally cylindrically shaped. The distal end of body 44 is open as represented by a dashed line opening 45 in FIG. 2. This allows the proximal end of the chuck 60 to be seated in the body 44. The drive spindle 48 extends into the open distal end of the handpiece.

Handpiece motor 46 is any suitable motor for actuating the cutting accessory. Motor 46 is typically an electrically pneumatically or hydraulically drive motor. A cable 43 is seen extending from the proximal end of handpiece body 44. Cable 43 represents that the power, gas or water used to drive the motor comes from a console separate from the system 40 of this invention. One such motor that can be incorporated into handpiece 42 is disclosed in the Applicant's U.S. Pat. No. 8,597,316, issued 2 Dec. 2013, CUTTING ACCESSORY FOR USE WITH A MEDICAL/SURGICAL POWERED HANDPIECE, THE ACCESSORY HAVING FEATURES THAT FACILITATE THE FINE OR COARSE ADJUSTMENT OF THE EXTENSION OF THE ACCESSORY SHAFT, the contents of which are incorporated herein by reference. A console that can be used to provide electrical power to an electrically driven motor is disclosed in the Applicant's U.S. Pat. No. 7,422,582, issued 9 Sep. 2008, CONTROL CONSOLE TO WHICH POWERED SURGICAL HANDPIECES ARE CONNECTED, THE CONSOLE CONFIGURED TO SIMULTANEOUSLY ENERGIZE MORE THAN ONE AND LESS THAN ALL OFF THE HANDPIECES, the contents of which are incorporated herein by reference. Again, it should be understood the structure of the handpiece motor 46 and the assembly, that powers the motor are not part of the present invention.

The drive spindle 48 is rotatably mounted in the body 44 by bearings not illustrated and not part of the invention. The drive spindle 48 is accessible through the open end 45 of the handpiece body 44. The drive spindle is formed to have a rectangular closed end bore 49 that opens from the distal end of the spindle and extends proximally therefrom.

Figure 3:
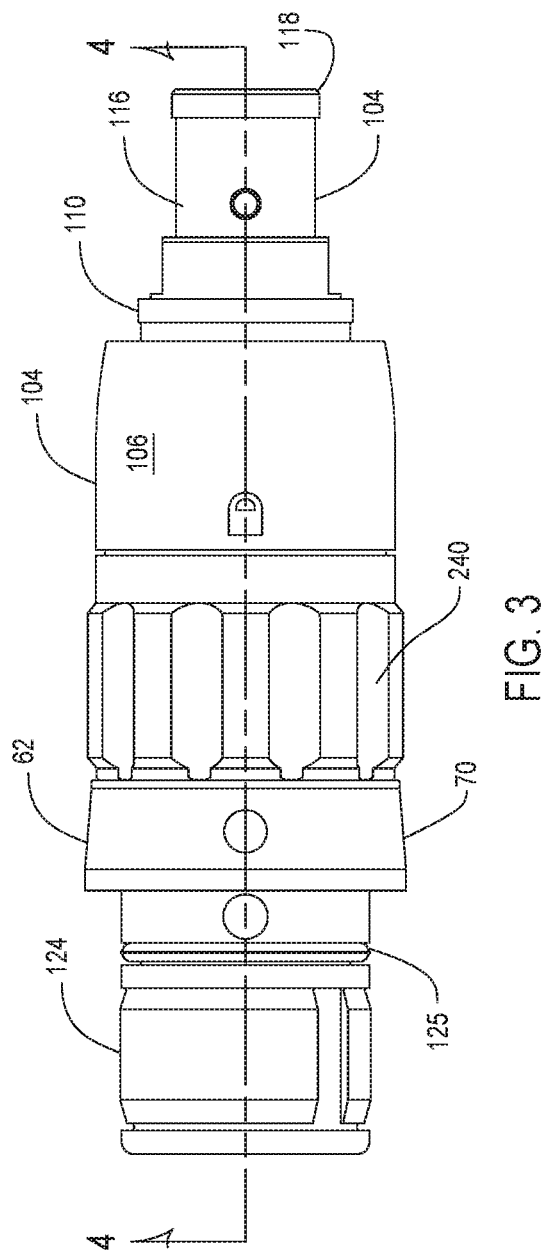
FIG. 3 is a plan view of the removable chuck of this system.
Figure 4:
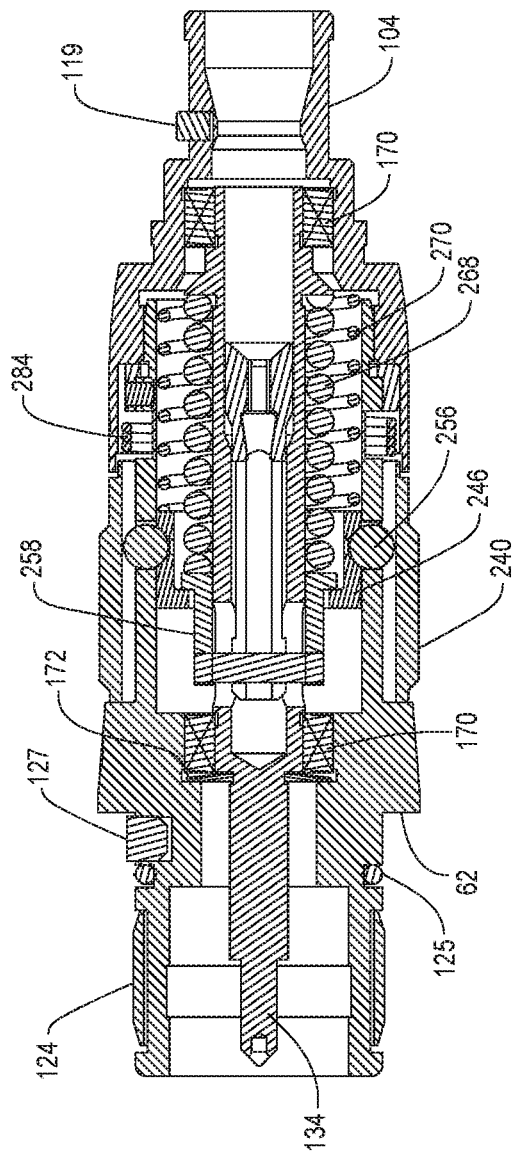
FIG. 4 is a cross sectional view of the chuck.
Figure 5:
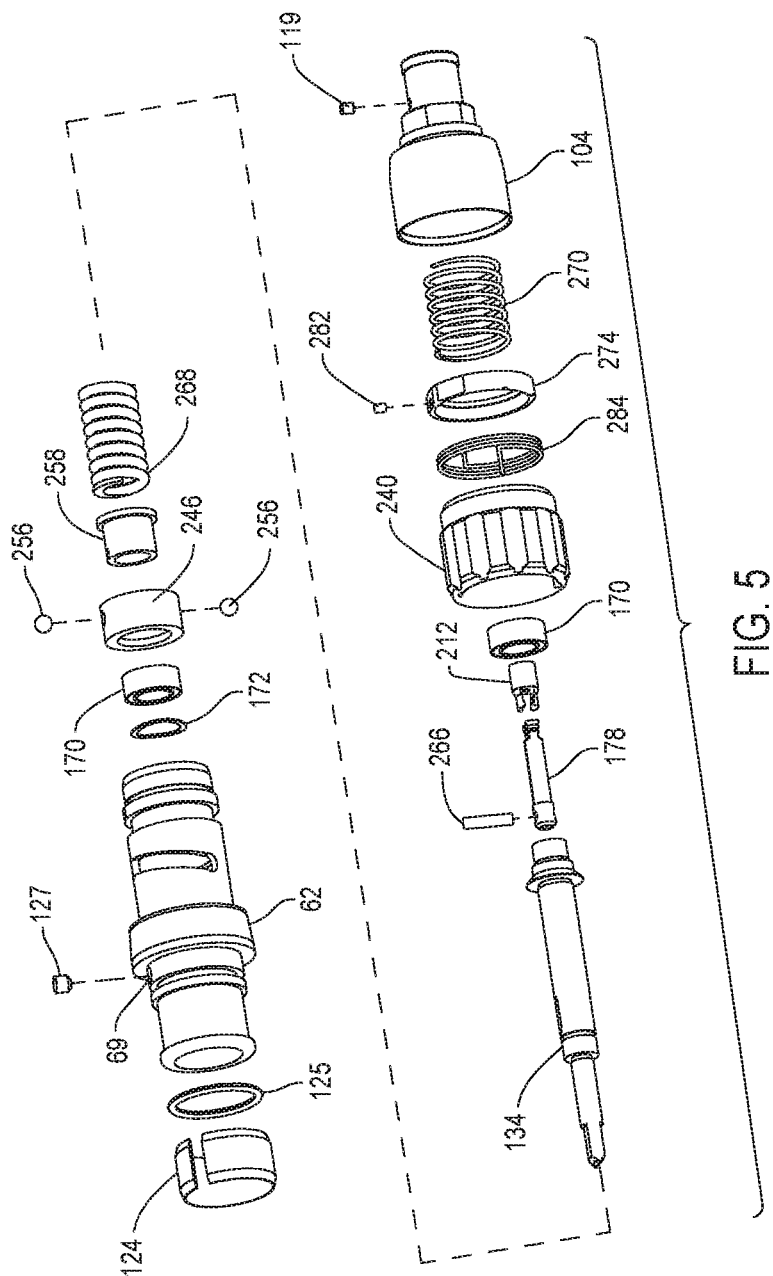
FIG. 5 is an exploded view of the chuck.
Figure 6:
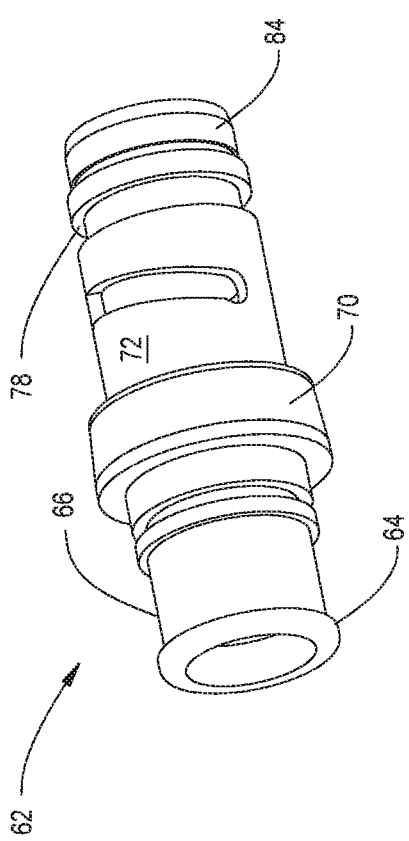
FIG. 6 is a perspective view of the body of the chuck.
Figure 7:
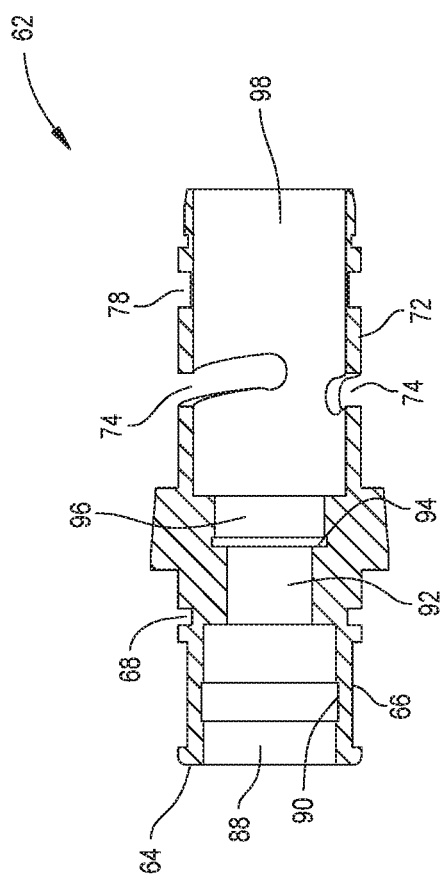
FIG. 7 is a cross sectional view of the chuck body.
Figure 8:
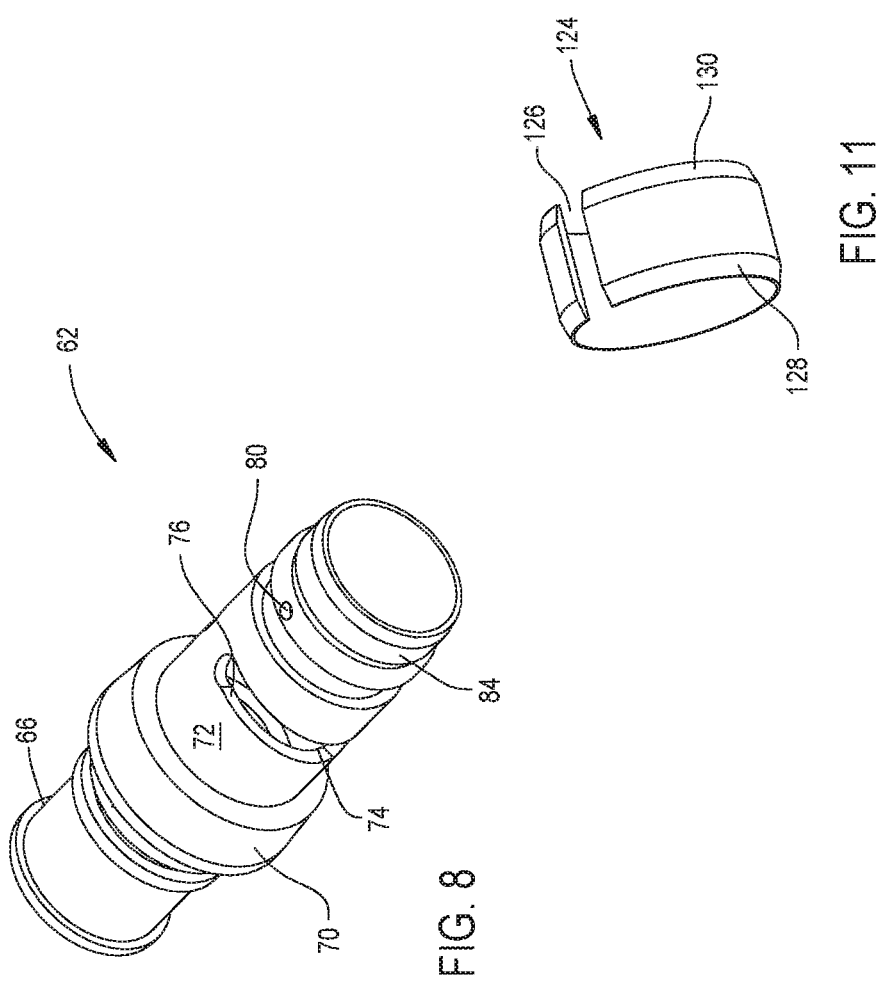
FIG. 8 is a an alternative perspective view of the chuck body.

Chuck 60 is formed to have a shell 62 and a cap 104, seen in FIGS. 3-5, that collectively form the body of housing of the chuck. Shell 62, seen best in FIGS. 6-8, is formed from a single piece of metal that generally has a number of different cylindrical sections. One proximal cylindrical section is a foot 64. Foot 64 is formed with two indentations that extends inwardly from the outer surface of the foot and circumferentially around the foot. A first one of these indentations is annular recess 66. The second indentation is a groove 68. In cross section, both recess 66 and groove 68 are rectangular in shape. The shell 62 is formed so that groove 68 is spaced forward from recess 66 and is shorter in length than the recess. A bore 69, partially seen in FIG. 5, extends laterally inwardly from the outer surface of foot. Bore 69 is located distally forward of groove 68. Forward of the foot 64, the shell 62 has a collar 70. Collar 70 has an outer diameter larger than the outer diameter of foot 64. In the depicted version of the invention, the outer diameter of collar 70 is tapered. Extending distally from the proximal end of the collar 70 the diameter of the collar slightly decreases.

Forward of collar 70, shell 62 has a head 72. Head 72 generally has a diameter approximately equal to the diameter of foot 64. Forward of the proximal end of the head 72 the head is formed to have helical slots 74. Slots 74 are symmetric around the proximal-to-distal longitudinal axis through the shell 62. The shell 62 is further formed so that adjacent each slot 74 there is a detent 76 (one seen in FIG. 8). Forward of where slots 74 are resent in the head 72, the head is formed to have a circumferentially extending recess 78. In the portion of head 72 forward of the recess 78 a bore 80 extends laterally through the head.

A lip 84 extends forward from head 72 and forms the most distal portion of shell 62. Lip 84 has an outer diameter that is less than that of the head 72. Lip 84 is formed with threading, (not illustrated).

The shell 62 is formed to have a number of contiguous bores that form a channel that extends longitudinally through the shell. A first bore, bore 88, extends distally forward from the proximal end of the shell. Bore 88 is thus located in the shell foot 64. Shell 62 is further formed so that the inner wall of the shell that defined bore 88 has a recess 90 that extends circumferentially outward from bore 88. Recess 90 is contiguous with bore 88 and is located approximately in the middle of the bore. Recess 90 extends circumferentially around bore 88.

A bore 92 extends distally forward from the distal end of bore 88. Shell 62 is formed so that bore 92 is located within the shell collar 70. Bore 92 has a diameter less than that of bore 88. The distal end of bore 92 opens into a bore 96. Bore 96 has a diameter less than that bore 88 and greater than that of bore 96. The shell 62 is further formed so as to define a groove 94 in the inner wall of the shell that defines bore 96. groove 94 extends outwardly from the proximal end of bore 96 where bore 88 opens into bore 96. Groove 94 extends circumferentially around the outside of bore 96. A bore 98 extends from the distal end of bore 96 to the distal end of the shell 62. Bore 98 has a diameter that is greater than the diameter of shell bore 88. The shell 62 is formed so that bore 98 extends through both the shell head 72 and distal end lip 84.

Figure 9:
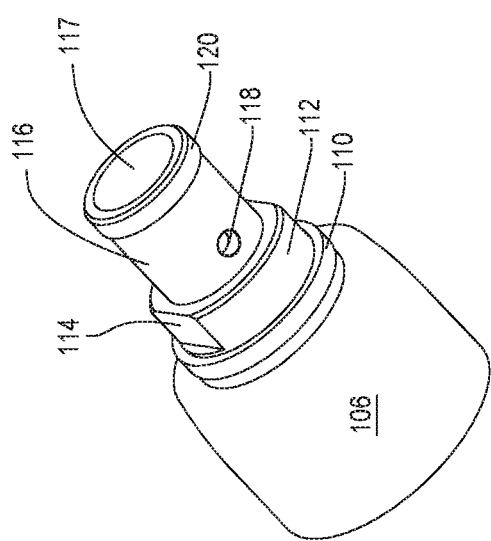
FIG. 9 is a perspective view of the chuck cap.
Figure 10:
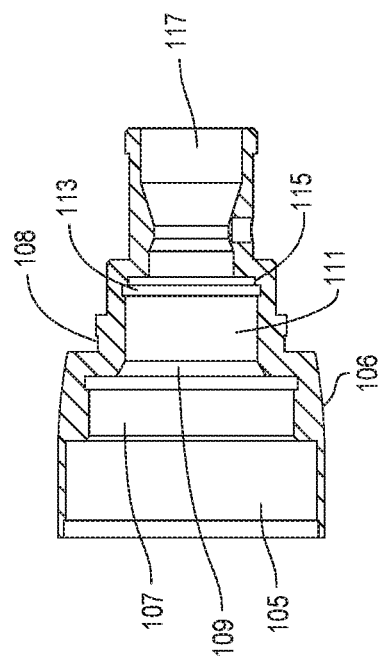
FIG. 10 is a cross sectional view of the chuck cap.

Cap 104, now described with reference to FIGS. 9 and 10, has a base 106. Base 106 is generally circular in cross section. The cap 104 is further formed so that as the base 106 extends distally, there is a slight decrease in the outer diameter of the base. Forward of base 106 the cap has a collar 110. Collar 110 is generally cylindrical and has a diameter less than that of the base. Cap 104 is further shaped so that the portion of collar 110 immediately forward of base 106 has a recess 108. The recess 108 extends circumferentially around the collar 110.

A neck 112 extends distally forward from the cap collar 110. The neck 112 has a curved outer surface that has a diameter less than that of collar 110. The outer surface of the neck 112 is not completely cylindrical. Instead, the neck 112 is formed to have two parallel diametrically opposed flats 114. Flats 114 are located inward of the connecting outer curved sections of the neck 112.

A cylindrical head 116 extends forward from collar 110. Head 116 has a diameter less than then distance across the neck flats 114. A short distance, approximately 4 mm, forward of the proximal end of the head a bore 118 extends laterally through head. Bore 118 extends into the below described bore 117. At the distal end of the head 116 there is a rim 120. Rim 120 protrudes radially outwardly from head 116.

A bore 105 extends distally forward from the proximal end of cap base 106. Bore 105 has a diameter greater than that of shell head 72. The distal end of bore 105 opens into a bore 107. Bore 107 has a diameter less than that of bore 105. The inner cylindrical wall of the cap 104 that defines bore 107 is formed with threading (not illustrated). More particularly the cap bore 107 is dimensioned to accommodate shell lip 84 so that complementary threading around shell lip 84 and the bore engage. A bore 109 extends forward from bore 107. Bore 109 has a diameter less than that of bore 107. Not identified is the undercut between bores 107 and 109. Bore 109 is tapered. Thus, extending distally from bore 107, the diameter of bore 109 decreases.

The distal end of bore 109 opens into a bore 111. Bore 111 is cylindrical in shape and has the same diameter as the diameter of the distal end of bore 109. Bore 111 opens up into a bore 115. Bore 115 has a diameter less than that of bore 111. An undercut 113 is located between bores 111 and 113.

Forward of bore 115, a bore 117 extends through cap head 116. Bore 117 has sections with varying diameters. Cap head 116 including bore 117, is formed to receive components 308 internal to the nose 302 that serve to releasably hold the nose to the chuck 60.

A pin 119 is seated in cap bore 118. Pin 119 (FIG. 4) cooperates with the nose coupling features 308 to hold nose 302 to chuck 60.

A flexible spring ring 124, best seen in FIG. 11, is snap fitted in recess 66 formed in shell foot 64. The spring ring 124 is generally in the form of a cylindrical sleeve that has a break 126 that extends the length of the ring. The spring ring is formed so that, at the proximal and distal ends of the ring, the outer surfaces 128 and 130, respectively of the ring taper inwardly. The components forming system 40 are dimensioned so that when the ring 124 is seated over chuck foot 64, the major outer annular surface 129 of spring ring 124 the ring protrudes outwardly from the foot. This facilitates the snap fitting of the ring in and out of opening 45 internal to the handpiece body 44. Not illustrated are the structural features internal to the handpiece body 44 that against which the spring ring abuts 124. These surfaces are the surfaces that restrain movement of the spring to facilitate the releasable attachment of the chuck 60 to the handpiece 42.

An O-ring 125, seen in FIG. 5, is seated in shell groove 68 and protrudes out of the groove. The O-ring 125 damps vibration of the chuck 60 relative to the handpiece. A pin 127 is seated in shell bore 69 and protrudes out of the bore. The pin 127 cooperates with the components internal to handpiece body 44 to prevent the rotation of the chuck 60 relative to the handpiece 42. The components internal to the handpiece body that pin 127 engages are not part of the current invention.

As seen best in FIGS. 12 and 13, the chuck drive shaft 134 is a single piece unit. At the proximal end the drive shaft is formed to have a leg 136. Leg 136 is generally cylindrical. At the proximal end of the shaft 134, leg 136 is formed to have two parallel flats 138 (one seen) extend forward from the proximal end of the leg. The proximal portion of the leg, the portion in which the flats 138 are present, is dimensioned to slip fit in the handpiece drive spindle bore 49 so there is a minimal clearance between the spindle 48 and the drive shaft leg. Not identified but visible in FIGS. 12 and 13 is a bore that extends distally forward from the proximal end of drive shaft 134. This bore is not part of the current invention.

Forward of leg 136, the drive spindle has a waist section 139. Waist section 139 is cylindrical in shape and has a diameter greater than that of leg 136. Forward of the waist section the drive shaft has a torso 142. Torso 142 is cylindrical in shape and has a diameter greater than that of the waist section 139. An undercut 144 present for manufacturing purposes separates the waist section 139 and the torso 142. An undercut 140, also present for manufacturing reasons, separates leg 136 from waist section 139. Forward of undercut 144, the torso 142 is formed with two symmetrically opposed oval shaped openings 146. Torso 142 is shaped so that the major axes of openings 146 are parallel to the proximal to distal longitudinal axis through drive shaft 134.

The drive shaft 134 is further formed to have a neck 150 that is located immediately forward of the distal end of the torso 142. Neck 150 protrudes radially outwardly from torso 142. Not identified is the undercut in the torso 142 immediately proximal to the neck 150. Neck 150 has a proximally facing outer surface 152

Forward of the neck 150, drive shaft 134 has a head 158. Head 158 is cylindrical and shape. The head 158 has a diameter equal to or less than that of shat torso 142.

A bore 162 extends proximally rearward from the distal end shaft head 158. Bore 162 extends through the shaft head 158 and neck 150 and partially through the torso 142. The proximal end of bore 162 opens into a bore 166. Bore 166 is coaxial with and smaller in diameter than bore 162. A step 164 at the proximal end of bore 162 defines the transition between bore 162 and bore 166. Bore 166 terminates at a location forward of the proximal end of the shaft torso 142. Torso openings 146 open into bore 166.

Two bearing assemblies 170, seen in FIGS. 4 and 5, rotably hold the drive shaft 134 to the chuck housing. (Not illustrated with specificity are the inner and outer races of the bearing assemblies 170. The inner race of the proximal located bearing assembly 170 is disposed over waist section 139 of the drive shaft 14. The outer race of the proximal located bearing assembly 170 is seated against the inner wall of shell 62 that defines bore 96. A wave washer 172 (FIG. 5) is located immediately proximal to the proximal end of proximal bear assembly 170. The outer perimeter of the wave washer 172 is seated in shell groove 94. The inner perimeter of the wave washer is seated in drive shaft groove 140. Wave washer 172 bears against the drive shaft 134 so as to urge the drive shaft distally forward.

The inner race of the distal bearing assembly 170 is seated around the drive shaft head 158. The outer surface of the bearing assembly is disposed against the inner cylindrical wall of the cap 106 that defines bore 111. The components forming chuck 60 are dimensioned so that distal end of the drive shaft is spaced rearward of undercut 113 internal to cap 106.

Figure 14:
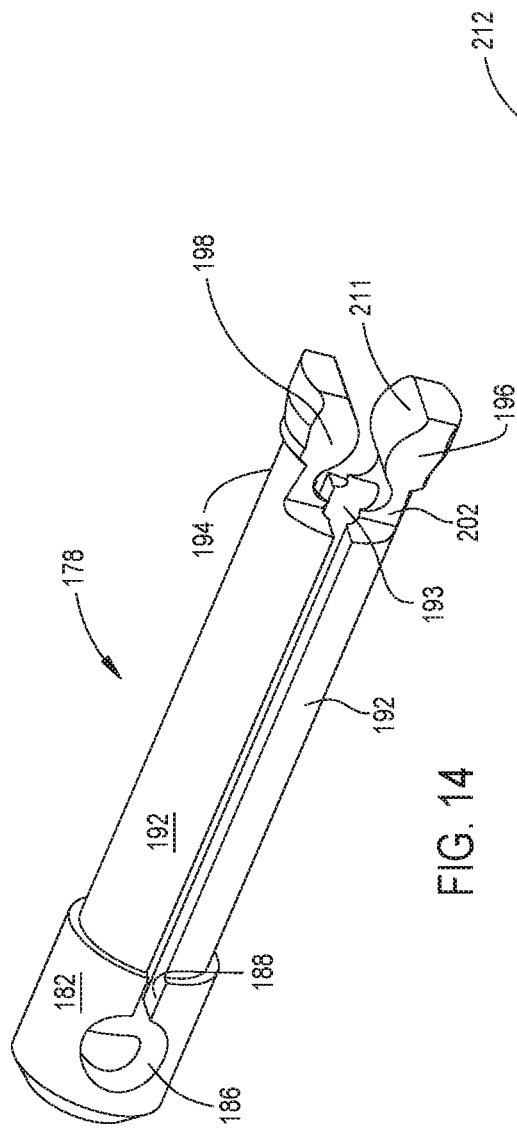
FIG. 14 is a perspective view of the collet.
Figure 15:
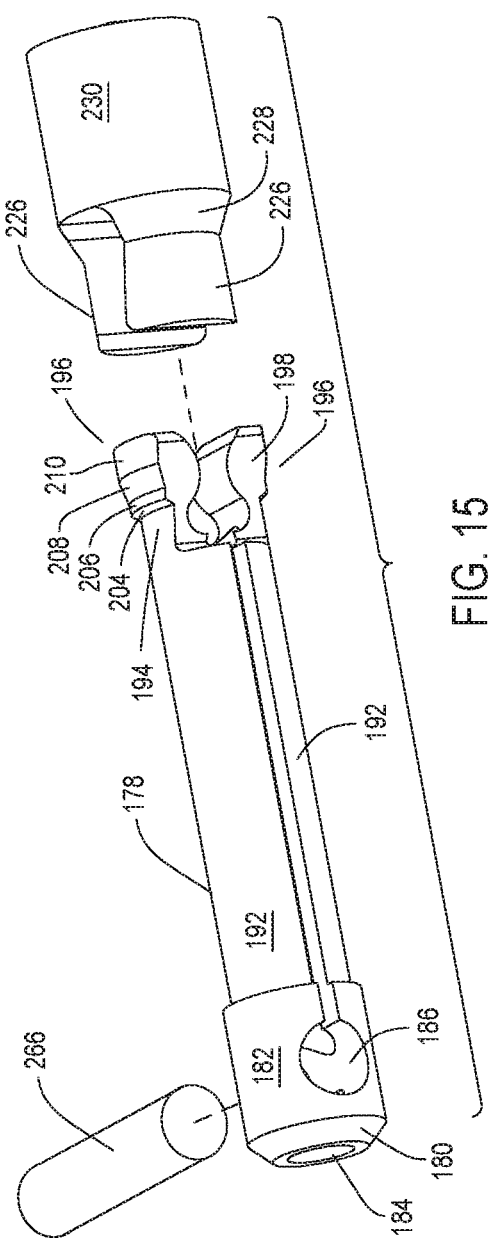
FIG. 15 is an exploded view of the collet, the alignment collar and the drive pin.

A collet 178, now described by reference to FIGS. 14 and 15, is slidably disposed in drive shaft 136. Collet 178 releasably holds the cutting accessory 320 to the drive shaft. The collet 178 is single piece component that includes a base 182. Base 182 is cylindrically shaped and is dimensioned to slidably fit with minimal lateral movement within drive shaft bore 166. A crown 180 extends proximally forward a short distance from the proximal end of the collet base 182. Crown 180 is tapered such that extending proximally from the base 182 the diameter of the outer surface of the crown decreases. A bore 184 extends longitudinally through the crown and base 182. Bore 184 is present for manufacturing reasons. The presence of bore 184 also facilitates flexure of collet legs 192 discussed below. A bore 186 extends laterally, side-to-side through the collet base 182. Bores 184 and 16 intersect. The collet 172 is formed so that a slot 188 extends distally forward from bore 188. Slot 188 is located on a proximally to distally extending plane in which the center longitudinal center axis of the collet lies 178.

Two legs 192 extend forward from the collet base 182. Legs 192 are arcuately shaped. The circle defined by the outer surfaces of the legs has a diameter less than the diameter of base 182. The circle defined by the facing opposed inner surfaces of the legs defines a void 193 the distal end of which is identified in FIG. 14. In cross section in planes perpendicular to the longitudinal axis, void 193 is generally circular in shape.

An ankle 194 and a foot 196 are located at the distal end of each leg 192. Each ankle 194 has an outer surface that is flush with the outer surface of the leg from which the foot extends. As discussed below, the feet 196 have outer surfaces that extend radially outwardly from the outer surface of the ankles 194. Each ankle 194 and foot 196 has a pair of opposed sides 198. The ankle 194 and foot 196 are shaped so that the sides 198 taper relative to a proximal to distal longitudinal axis through the ankle and foot. Thus, immediately adjacent the leg from which the ankle 194 extends the distance between opposed sides 198 is relatively short, less than the distance across the leg. Extending distally, the distance between sides 198 of a single foot 196 increases. Thus on each side of the collet 178 the adjacent side surface of the opposed ankles and feet define a notch 202, one identified in FIG. 14. Each notch 202 has a shape such that the width across the notch decreases distally along the notch. Notches 202 can be considered to nave a curved dovetail shape.

Each foot 196 has four arcuately shaped outer surfaces first outer surface, surface 204, extending distally from the ankle, tapers outwardly as the surface extends distally that the surface approaches being perpendicular to the longitudinal axis through the collet 178. The second surface, surface 206, has a radius of curvature that is essentially constant along the length of the surface 206. The third surface, surface 208, extending distally, tapers out slightly from surface 206. Surface 208 tapers to the fourth surface, surface 210. Surface 210 has a constant diameter. The circle defined by the opposed surfaces 210 has a diameter that is approximately 0.12 mm less than the diameter of drive shaft bore 162. This dimensioning allows the collet legs 192, ankles 194 and feet 196 to flex outwardly away from the longitudinal axis that extends through the drive shaft 136.

Each foot 196 projects inwardly towards the longitudinal axis of the collet 178 and the opposed foot 196. The inner most surface of each foot is considered the toe surface 211. Toe surfaces 211 are each convex in shape.

Also slidably disposed in the drive shaft 136 is an alignment collar 212, described with reference to FIGS. 16-18. Alignment collar 212 has a head 230 with a cylindrical shape. More particularly, head 230 is dimensioned to move longitudinally in drive shaft bore 162. A waist 228 is located proximally rearward from head 230. Waist 228 is shaped to, extending proximally from head 230, taper inwardly. A pair of opposed feet 226 extend outwardly from waist 228. Feet 226 and waist 228 are collectively shaped to define a notch 229 that extends distally from the proximal end of the collar 212. Notch 229 is dimensioned to receive the opposed collet ankles 194 and feet 196.

Alignment collar 212 is further formed to have an opening 232 that extends proximally inwardly from the distal end of the collar. Opening 232 is tapered. As the opening 232 extends proximally from the distal end of the head 230, the diameter of the opening 232 decreases. Opening 232 terminates at a bore 234 that is cylindrical in shape. The proximal end of bore 234 opens into a bore 236. In cross section, in planes perpendicular to the longitudinal axis through the alignment collar 212, bore 236 is in the shape of flattened oval. More particularly, bore 236 has two opposed parallel sides. Two curved ends connect the parallel sides. Each curved end subtends an arc of approximately 120°. Two steps, identified only in FIG. 18, at the base of bore 234, define the transition between bore 234 and bore 236. Bore 236 occupies a length that is approximately two-thirds the total length of the collar head 232. Bore 236 opens into notch 229.

When chuck 60 is assembled, the base and legs of collet 178 are seated in drive shaft bore 166. Collet ankles 194 and feet 196 are disposed in collar notch 229. Also disposed in collet bore 162 is alignment collar 212. Each collet ankle 194 and associated foot 196 is disposed in an end of alignment collar notch 229 as seen in FIGS. 15 and 15A. Collet 178 and alignment collar 212 are, as seen best in FIG. 15A, are further formed so that when the collet and ankles 194 and feet 196 are seated in the collar notch 229, the ankles and feet are spaced away from the adjacent notch-defining surfaces. There is a narrow separation between the collet side surfaces 198 and the adjacent surfaces of the alignment collar 212. There is wider gap between the distal end surfaces of the collet feet 196 and the adjacent surfaces of the alignment collar. The depicted gaps are enlarged for purposes of illustration. It should be understood that collet feet 196 are able to flex laterally relative to the alignment collar feet 226.

A number of components of the chuck cooperate to move collet 178 and alignment collar 212 longitudinally within the drive shaft. One of these components is a lock ring 240 now described by reference to FIG. 19. Lock ring 240 is sleeve like in shape. The lock ring 240 has an inner diameter that allows the ring to slip fit and rotate over shell head 72. The outer surface of the lock ring 240 is formed with knurling 242 to allow easy thumb and finger rotation of the ring. The knurling 242 extends along approximately the proximal most four-fifths of the ring. The distalmost one-fifth of the ring is smooth.

Lock ring 240 is further formed so that two grooves 244 extend inwardly from and longitudinally along the inner wall of the ring. Grooves 244 are symmetric with respect to the proximal-to-distal longitudinal axis through the ring 240. In cross-section, in planes perpendicular to the longitudinal axis through the lock ring, grooves 244 are curved in shape.

Figure 21:
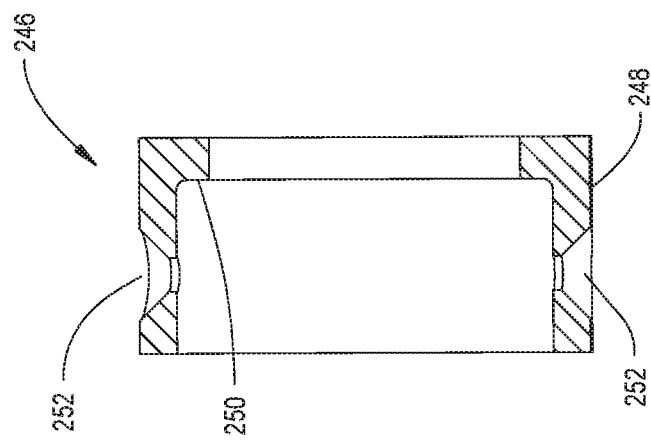
FIG. 21 is a cross sectional view of the actuator.
Figure 20:
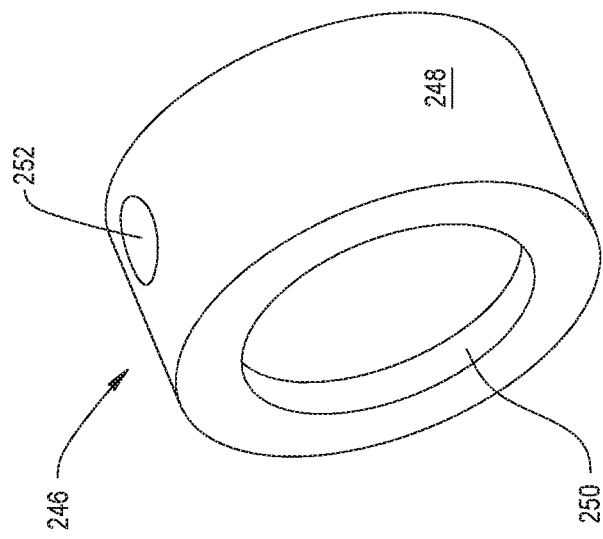
FIG. 20 is a perspective view of the actuator internal to the chuck.
Figure 25:
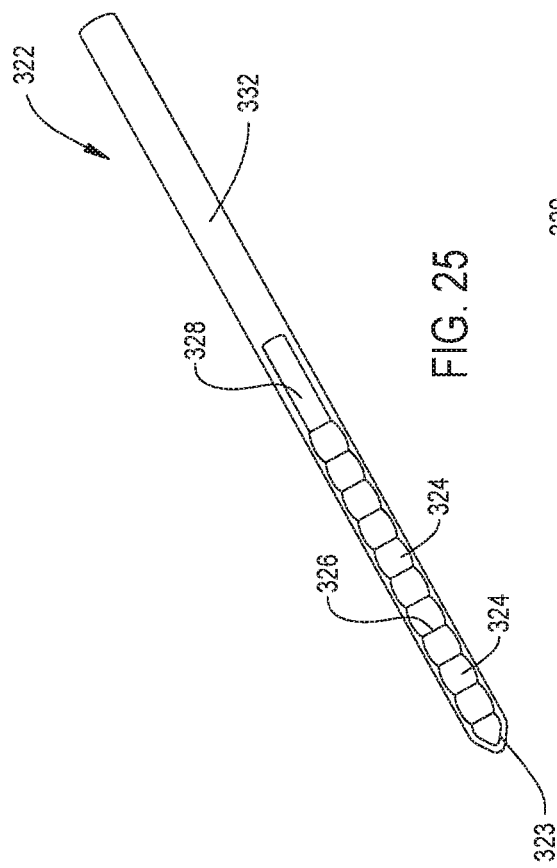
FIG. 25 is a perspective view of the distal end of a cutting accessory shaft.
Figure 26:
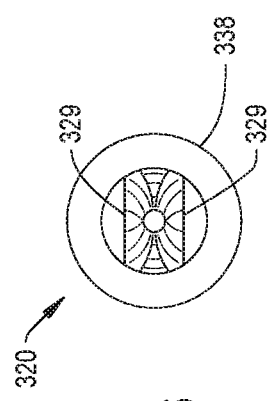
FIG. 26 is a plan view of the proximal end of the cutting accessory looking distally forward.
Figure 27:
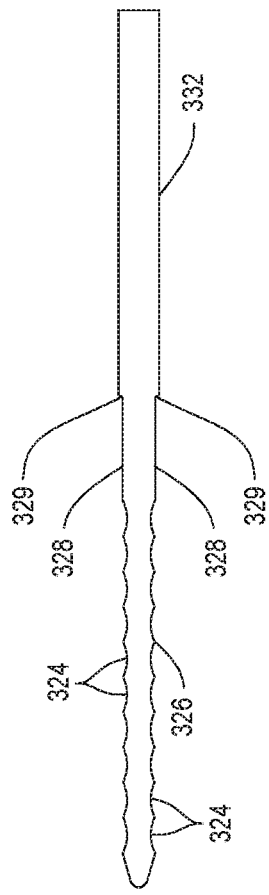
FIG. 27 is a plan view of the proximal end of the cutting accessory shaft wherein the side edges of the retention features are seen.

An actuator 246, seen best in FIGS. 20 and 21, is a second component that is part of the assembly that longitudinally translates the collet 178 and alignment collar 212. The actuator 246 has a sleeve like main body 248. The outer diameter of the actuator main body 248 is dimensioned to allow the actuator to engage in close longitudinal slip fit movement within shell bore 98. At the distal end of the main body 248, actuator 246 has a lip 250 that extends radially inwardly from the main body. The actuator 246 is further dimensioned so the inner diameter of lip is approximately 2.5 mm greater than the outer diameter of the drive shaft torso 142.

Actuator 246 also has two symmetrically opposed divots 252. Each divot 252 is a void space in the form of a slice section of sphere. Each divot 252 is shown opening into the interior of the actuator 246. This opening is present for manufacturing reasons.

When chuck 60 is assembled, the actuator 246 is seated in shell bore 98. A ball bearing 256, seen best in FIG. 5, is seated in each of the shell helical slots 74. The ball bearing 256 is dimensioned to project outwardly from both the outer and inner surfaces of the shell head 72. The portion of each ball bearing 256 that projects outwardly from the shell head seats in one of the lock ring grooves 244. The portion of each ball bearing 256 that projects inwardly of the bore 98 defining inner surface of the shell is seated in one of the divots 252. Thus, the rotation of the lock ring causes the ball bearings 256 to move longitudinally along the shell in the groove 244. The longitudinal movement of the ball bearings 256 causes the actuator 246 to move longitudinally in the shell bore 98.

A drive link 258, seen best in FIG. 22, is also slidably disposed in the shell bore 98. The drive link 258 has a tube like main body 260. The outer surface of main body 260 as a diameter less than the inner diameter of actuator lip 250. The inner surface of the main body 260 has a diameter sufficiently greater than that of the drive shaft torso 142 that the drive link can freely move longitudinally over the drive shaft 134.

Drive link 258 has a rim 262 that extends radially outwardly from the main body 260. Rim 262 is located at the distal end of the main body 260. The drive link 258 is further formed to have two coaxial bores 264. Bores 264 are located forward of the proximal end of the body. The common axis around which bores 264 is centered intersects the proximal-to-distal longitudinal axis through the drive link 258.

The drive link 258 is disposed over dive shaft torso 142 to move over the torso. Drive link 258 is positioned so that drive link rim 262 is located immediately distally forward of the actuator lip 250. The components forming the chuck are dimensioned so that the drive link rim 262 projects over the actuator lip 250.

The components forming chuck 60 are further arranged so that drive shaft openings 146, collet bore 186 and drive link bores 264 are in registration. A drive pin 266, identified in FIGS. 5 and 15, extends through these voids. The drive pin 266 is tightly fitted in the collet bore 186 and the drive link bore 264. Drive pin 266 is able to move proximally and distally within drive shaft openings 146. The drive pin 266 transfers the rotational motion of the drive shaft 134 to the collet 178. Drive pin 266 also transfers the longitudinal movement of the drive link 258 to the collet 178 so that that collet moves in unison with the drive link.

Two coil springs 268 and 270, seen in FIGS. 4 and 5, are disposed around the drive shaft torso 142. A first spring, spring 268, is in terms of radial distance, is located closest to the outer cylindrical surface of the torso 142. The proximal end of spring 268 abuts the rim 262 of drive link 258. The distal end of spring 268 abuts the annular proximal facing surface 152 of the drive shaft neck 150. Spring 268 is in compression. Spring 268 thus normally exerts a force that holds the drive link 258 proximally away from the drive shaft neck 150. The force exerted by spring 268 can be overcome by the manual force that causes the longitudinal translation of the drive link.

Spring 270 is located outwardly of and surrounds spring 268. The proximal end of spring 270 is disposed against the ring shaped, distally directed surface of the actuator 246. The opposed distal end of the spring 270 is disposed against the ring shaped step internal to the cap 104 that is the transition between bores 107 and 109.

Also disposed inside the hub is a stop ring 274 seen in FIG. 23. As implied by its name, stop ring 274 is ring shaped. The stop ring 274 is formed with a number of sections with flat outer faces 276. One outer face 276 is formed with an opening 278 that extends through the ring towards the center of the ring 274. Stop ring 274 is further formed so as to nave a closed end bore 280 that extends proximally from the distally proximally directed face of the ring.

Stop ring 274 is fixedly disposed in chuck 60 over the portion of shell head 72 forward of recess 78. A pin 282 (FIG. 5) that extends through lock ring opening 278 into shell bore 80 holds the stop ring fast to the shell 62.

A coil spring 284, seen in FIGS. 4 and 5, is located immediately proximal to stop ring 274. Spring 284 has two opposed legs (not identified). A first leg extends proximally and is disposed bore formed in the lock ring 240 (bore not seen). The second leg extends distally and extends into stop ring bore 280. Spring 284 places a force of lock ring 240 that opposes the rotation of the lock ring. The force spring 284 place on the lock ring 240 can be overcome by the finger force applied to the lock ring 240 to rotate the lock ring.

The nose 302, as seen in FIGS. 2 and 24, includes a base 304. Base 304 is generally tapered in shape in that, extending from the proximal end the outer surface, the diameter of the base decreases. There are portions 304 of the base that are of constant diameter. The inside of the base 304 has a void 306 and coupling features 308. Void 306 and coupling features 308 are designed, to facilitate the releasable coupling of nose base 304 over cap head 116 and neck 112. The specific means by which the nose is coupled to chuck 60 are not part of the present invention. Accordingly, void 306 and coupling features 308 are not further described.

A constant diameter tube 310 is mounted to and extends distally forward of nose base 302. The distal end of the lumen 312 internal to the tube opens into base void 304. Inside the lumen 312 there are bearing assemblies 314. Bearing assemblies 314 rotatably hold the shaft, 322 integral with cutting accessory in the tube lumen 312.

While tube 310 is depicted as being straight, it is understood that this invention is not so limited. In alternative versions of the invention the tube is curved, the proximal to distal longitudinal axis bends. This makes it possible for the surgeon using the system to position the distal end of the tube as well as the attached accessory tissue working member 338 at a location that is shifted radially away from the a line that consist of an extension of the proximal-to-distal longitudinal axis through the handpiece 42. This positioning facilitates placement of the tissue working member against the side of the tissue that defines the portal into the patient into which nose tube 310 is inserted.

The structure of a cutting accessory 320 is understood by reference to FIGS. 2 and 25-27. A cutting accessory includes an elongated shaft 322. A tissue working member 338 is attached to the distal end of the shaft 322. The tissue working member is designed to accomplish a procedure on the living tissue against which the tissue working member is applied. The depicted tissue working 338 member is a bur. (Cutting flutes of the bur not illustrated.) The specific structure of the tissue working member 338 is not part of the present invention. In alternative versions of the invention, the tissue working member may be a bur with a head that has a shape that is not spherical. Alternatively, the tissue working member may be a drill bit. It Accessory shaft 322 is generally in the form of a cylindrical rod. In some versions of the invention shaft 32 is formed out of 142 tool steel or 440A stainless steel. Adjacent the tissue working member 338, shaft 322 has a distal section. 334 that is relatively inflexible. Shaft distal section 334 has a length between 1 and 3 cm. Proximal to distal section 334, shaft 322 has a proximal section 332. Shaft proximal section 332 is smaller in diameter than shaft distal section 330. This reduced diameter or the proximal section 332 allows the proximal section to, when inserted in a curved or angled nose tube flex. Shaft proximal section 332 has a diameter of 2 mm or less and often a diameter of 1.6 mm or less.

The accessory shaft 322 is further formed so that there is a taper 323 at the most proximal end of the shaft. Thus, extending distally from the most proximal end of the shaft 322, the diameter of the shaft increases. Shaft 322 is further formed to have on diametrically opposed sides of the shaft, plural faces 324. Faces 324 are arranged longitudinally along the shaft and extend forward from the tapered sections of the shaft. In the illustrated version of the invention each face is concave. Each face 324 is arcuate in shape and curves inwardly from the outer cylindrical surface of the shaft proximal section 332. At the most proximal end there are not two full faces. Each face 324 at the proximal end, extending distally from that end curves outwardly towards the adjacent distally located face. At the location where there two longitudinally adjacent faces abut there is crest 326, one identified in each of FIGS. 25 and 27. Crests 326 appear as lines.

On each side of the shaft 322, the set of faces appear as a row of faces. Accessory shaft 322 is further formed so that forward of the most distal face 324 face in each row of faces there is a flat 328. Each flat 328 is rectangularly shaped and recessed relative to the outer cylindrical surface of the shaft. Flats 328 are planar. The planes in which flats 328 lie are parallel to the longitudinal axis through shaft 322. Each flat 328 is located a distance away from the longitudinal axis of the shaft equal to the distance the crests are spaced from the shaft. A step 329 defines the transition of each flat 328 from the adjacent distally extending portion of the shaft proximal section 332. Steps 329 are in a plane that is generally perpendicular to the longitudinal axis through the shaft 322.

The components forming system 40 are shaped so that the radius of curvature of shaft 322 is typically between 0.01 and 0.02 mm less than the radius of the circle defined by the curved sides of alignment collar bore 236. The radius of curvature of the shaft is further understood to be approximately 0.2 to 0.4 mm less than the radius around the center of void 193 internal to the collet 178. The distance across the shaft flats 328 is 0.02 and 0.05 mm less than the distance across the parallel sides of collar bore 236. Shaft faces 324 are shaped so that each face can receive the outwardly curved face of one of the collet toe surfaces 211.

System 40 of this invention is prepared for use by first connecting chuck 60 to handpiece 42. The results in the coupling of the chuck drive shaft 134 to the handpiece spindle 48. Nose 302 is fitted over the chuck cap 104.

To couple the cutting accessory 320 to the rest of the system 40, the lock ring 240 is rotated to place the chuck in the load state. More particularly the lock ring 240 is rotated to cause the distal translational movement of actuator 246. The movement of the actuator lip 250 against rim 262 of the drive link 258 results in the like distal movement of the drive link. The distal translation of the drive link 258 results in the like distal movement of collet 178 such that that collet feet 196 are located forward of drive shaft step 164. When the collet 178 is so positioned, the collet feet 196 are free to flex outwardly. System 40 is in the load state.

At this time, the system 30 is in condition to receive the cutting accessory 320. The proximal end of the cutting accessory is inserted into the nose 302 and into the chuck. When the proximal end of the cutting accessory enters the alignment collar 212 the accessory may not be aligned with collar bore 236. In this situation, the proximal end of the accessory shaft 322 strikes the frustro-conically shaped surface of the alignment collar 212 that defines the collar opening 232. Owing to the presence of the taper of the surface of the collar that defines openings 232 and taper 323 of the shaft, the continued insertion of the accessory shaft 322 results in the lateral translation of the proximal end of the accessory toward bore 234. When the proximal end of the shaft enters collar bore 234, the shaft may not be aligned with the adjacent accessory bore 236. For these two components to be aligned, the accessory crests 326 should lie in planes parallel to the planes of the parallel sides of bore 236. In these components are not so aligned, the further advancement of the accessory is stopped by the abutment of the accessory around the step internal to the collar between bores 234 and 236. This blocking of the accessory advancement functions as a tactile cue to the individual performing this process that the accessory 320 needs to be aligned with the chuck 60. This alignment is easily performed by rotating the shaft, so the shaft is able to pass through the collar bore 236. Since the proximal end of the shaft is seated in bore 234 there is little likelihood that, as a result of this rotation of the shaft, the shaft will work itself out of bore 234.

Once the shaft 322 is properly aligned, the shaft is inserted into bore 236. The proximal section 332 of the shaft first transits in the space between collet toe surfaces 211 and enters the collet void 193. This movement is possible because, as the shaft crest 326 push against the toe surfaces 211, the collet feet 196 are free to flex outwardly. Again, there is a gap between the distal ends of the collet feet 196 and the adjacent proximally directed surfaces of the alignment collar 212 that define notch 229. The existence of this gap ensures that as the collet feet 196 flex, the flexure is not blocked by the abutment of the feet against the alignment collar. As the shaft 322 moves proximally the toe surfaces move in and out of engagement with the adjacent collet faces 324. Each time the collet feet ride flex outwardly over a pair of collet crests 326 there is a slight change in the resistance to the insertion of the shaft. This change in resistance provides tactile feedback that the shaft is going in and out of engagement with the collet feet 196.

Cutting accessory 320 is inserted in the chuck 60 until the tissue working member 338 is located forward the distal end of the nose 302 the distance desired by the practitioner. At this time, the collet toe surfaces 211 abut the opposed pair of shaft faces 324. The shaft is locked into position by rotating the lock ring 240 in the direction opposite the direction the ring is rotated to place the chuck in the load state. This opposed rotation of the ring 240 causes the ring to translate the actuator 246 proximally. Spring 268 is then freed to push the drive link 258 proximally. The proximal displacement of the drive link 258 causes a like proximal movement in the collet 178. More particularly, the collet 178 is displaced proximally until collet surfaces 206 abut step 164 internal to the drive shaft. This component against component abutment causes an inward movement of the collet feet 196 against the adjacent faces 196 of the cutting accessory 302. Chuck 60 is thus in the locked or run state.

As a result of the movement of the proximal movement or the collet, the collet abuts the angled stun surfaces of the alignment collar that define notch 229. Alignment collar 212 moves proximally with collet 178.

If necessary, cable 43 is connected to the console that provides power to handpiece motor 46.

System 40 is used by activating motor 46. The rotational moment of the handpiece drive spindle 48 is transferred to chuck drive shaft 134. Pin 266 transfers this rotational movement to the collet 178. Since the accessory shaft 320 is clamped between the collet feet 196, the accessory 320 undergoes a like rotation. The rotating tissue working member 332 is pressed against tissue in order to perform the desired surgical procedure.

As the cutting accessory 320 rotates, the crests 328 or flat 328 along one side of the shaft 322 presses against the adjacent planar surfaces of the alignment collar that defines bore 236. This surface-against-surface contact causes the alignment collar 212 to rotate with the accessory shaft 322. This also means there is a slight lag between the rotation of the collet 178 and the rotation of the alignment collar 212. As described above, the components forming chuck 60 are assembled so that there is a slight gap between sides 198 of the collet ankles 194 and feet 196 and the adjacent surface of the alignment collar. This gap prevents these surfaces from coming into contact when there is a lead or lag in the in the rotation of the collet 178 relative to the collar 212. This lead and lag occurs at system start up, system stop or when the accessory is driven back and forth in an oscillation mode. The prevention of this contact reduces the wear to which the collet and alignment collar would otherwise be exposed.

The components forming system 40 of this invention are thus designed to facilitate the easy coupling of the accessory 320 to the other components of the system, if the accessory shaft 322 is not aligned with the collet feet 198, the shape of the shaft and the alignment collar compel that, to further insert the shaft into the chuck, the shaft be rotated until the components are in alignment. The shape of these components lead the person setting up the system for use to so rotate the accessory shaft 322.

It is a further feature of this invention that the components of this invention are configured so that the accessory can be set so the distance the tissue working member 338 is set forward of the distal end of the nose 302 can be selectively set. This eliminates the need to provide plural different tissue working members the only difference between them being shafts of marginally different lengths.

Should a practitioner want the accessory set so the tissue working member 338 is set to the closest possible position relative to the nose 302, the shaft is disposed in the chuck so that shaft flats 328 are seated in the alignment collar bore 236. Further, should the person assembling the system 40 for use attempt to over insert the shaft in the collet, the steps 329 immediately forward of shaft flats 328 abut the alignment collar steps 235 around bore 236. This step-against-step abutment prevents insertion of the shaft beyond the useful depth of the shaft in the chuck 60.

Flats 328 provide a further advantage when present in some cutting accessories of this invention. Some cutting accessories 320 have tissue working members 338 that, when pressed against tissue are subjected to appreciable resistance by the tissue. One type of cutting accessory exposed to these loads are cutting accessories where the tissue working member a bur head with a diameter of 4 mm or greater. The concave shape of shaft faces 324 inevitably reduces the structural strength of the shaft proximal section 332. If the resistive load to which the rotating accessory is so great the reduced strength of this portion of the shaft could result in shaft fracture where these faces press against the walls of the alignment collet 212 that defines bore 236.

This class of cutting accessory 324 is instead provided with relatively few faces 324. This ensures that when the shaft is fitted to the chuck, a slice section of the flat 328-forming section of the shaft seats in collar bore 236. This slice section of the shaft 322 is of greater in cross sectional width than the section where concave faces are present. Stated another way, flats 328 are spaced further from the longitudinal axis of the shaft than the shallow portions of faces 324 are spaced from this axis. Alternatively, it can be stated that faces 324 extend inwardly relative to the flats 328. The slice section of the shaft 322 with flats 328, owing to its increased thickness, is better able to withstand the stress of the shaft-against-collar abutment that occurs when the accessory is subjected to appreciable resistance than the section of the shaft formed with faces 324. The ability of this section of the shaft to withstand this stress reduces the likelihood than owing to this resistance, the portion of the shaft disposed in the collet 212 can fatigue to the point of fracture.

It is a further feature of this invention that the advantages are provided in a system with components that are relatively small in cross sectional size. Nose tube 310 typically has a diameter of 0.3 cm or less and often 0.15 cm or less. As discussed above, the accessory shaft has a relatively small diameter so as to facilitate the insertion and flexing of the shaft in a nose with a curved tube 310. Thus, system 40 of this invention is designed to perform minimally invasive surgical (MIS) procedures.

The above is directed to one specific version of the invention. It should be understood that other versions of the invention may have features different from what has been described.

For example, there is no requirement that, in all versions of the invention, the chuck 60 be in a housing that is separate from and removable from the handpiece 42. In some versions of the invention, the chuck is built into the body of the handpiece. Further, in some versions of the invention there may not be a removable nose. In some versions of the invention where the nose is present the nose may, like the chuck be built into the handpiece. In still other versions of the invention, the nose and chuck may be a single piece assembly that is removably attached to the handpiece.

In some versions of this invention, the handpiece may have a transmission between the motor and the chuck drive shaft. One such transmission is present the transmission typically steps down the speed of the rotational moment so the chuck drive shaft rotates at a speed less than the speed of the rotor internal to the motor.

There is no requirement that all versions of the invention have cutting accessory shafts dimensioned and formed out of material that allow the shafts to flex. Alternative systems 40 of this invention may include cutting accessory that are formed with rigid shafts.

Likewise, the clamping assembly that releasably holds the accessory shaft to the drive shaft may not always be a collet with two feet. In other versions of the invention, the collet may have three or more feet that clamp against the accessory shaft 322. Further, in some versions of the invention, the clamping assembly might not include a collet. One such alternative clamping assembly is ball in hole assembly. This type of clamping assembly includes typically includes plural clamping balls. Each ball projects into a bore in the drive shaft. The bore receives the accessory shaft. When this type of chuck is in the locked state, the balls are held in the shaft bore. The balls engage complementary fastening features on the accessory shaft to clamp the accessory shaft for rotation to the drive shaft. When the chuck is in the load state, the balls are able to move radially in and out of the drive shaft bore. This allows the accessory shaft to be removed from the chuck. In some versions of the invention, this also allows the longitudinal position of the accessory 320 be selectively reset. In some embodiments of the invention there may be a single clamping member that holds the accessory shaft to the chuck drive shaft.

It follows from the above that there are variations to the geometry of the cutting retention features integral with accessory shaft 320 of this invention. There is no requirement that these features always be in the form of concave faces. For example, in some versions of the invention, these features may be convex faces. Alternatively, the features may be flats that are separated by laterally extending ridges. Still in other versions of the invention, these features may be flats formed with small pockets or indentations. The pocket or indentation (or plural pockets and indentations) formed with each retention feature would receive a complementary male feature of the chuck locking component. Similarly, from the above it should be clear that there is no requirement that in all versions of the invention the accessory shaft 322 be formed with two rows of symmetrically aligned retention features. In alternative versions of the invention, the accessory shaft 322 may have one row or three or more rows of retention features. In these versions of the invention there may be a flat associated with only a single one of the rows of the retention features. In versions of the invention where there are plural flats, the flats may not be symmetrically arranged around the longitudinal axis of the shaft 322. Alternatively, in some versions of arcuately adjacent flats may not be arcuately spaced apart from each other.

In some versions of the invention each flat 324 may not be aligned with a row of retention features 324. In this version of the system of this invention, the corresponding alignment collar face may not be aligned with one of the chuck clamping members.

Given that the chuck clamping assembly and the shaft retention features may be different from what has been described, it is inherent that the alignment collar 212 need not be as described above. Generally, the non-circular bore or opening of the alignment collar will have a shape that accommodates the non-circular cross sectional shape of the proximal end of the accessory shaft. This shape need not always be oval. The shape may be in the form of a truncated circle, a polygon or a circle with notch.

Further, the alignment collar may not always be a separate component from the other components of the chuck. In versions of the invention wherein the clamp assembly has the ball-in-hole locking elements, the alignment collar may be formed integral with the drive shaft. In these versions of the invention, the alignment collar thus defines a non-circular opening that leads to void internal to the drive shaft in which the accessory shaft is disposed and into which the locking balls move in and out.

The dimensions set forth above are for describing one version of the invention. Unless appearing in the claims the dimensions should be understood to not be limiting the scope of the claims.

Therefore, it is an object of the appended claims to cover all such variations and modifications that cover the true scope and spirit of this invention.

What is claimed is:

1. A cutting accessory for use with a powered surgical handpiece, the cutting accessory including:
   an elongated shaft having opposed proximal and distal ends, a longitudinal axis and an outer surface;
   a tissue working member attached to the distal end of the shaft, the tissue working member designed to accomplish a procedure on the living tissue against which the tissue working member is applied; and
   a proximal section that extends proximally from the distal end, the proximal section includes a plurality of faces that extend inwardly from the outer surface of the shaft, each face having at least one shallow portion and shaped to receive a clamping member that holds the shaft to the handpiece, wherein at least two of the faces are arranged linearly so as to extend proximally to distally along the shaft proximal section,
   wherein the shaft includes a flat that extends distally forward of the distalmost face such that no faces are distal the flat, the flat being located a distance from the shaft longitudinal axis that is greater than the distance shallow portions of the faces are located from the longitudinal axis and less than the distance the outer surface of the shaft is located from the longitudinal axis.

2. The cutting accessory of claim 1, wherein the flat is linearly aligned with the faces.

3. The cutting accessory of claim 1, wherein the shaft includes two rows of faces and a said flat extending forward of each row of faces.

4. The cutting accessory of claim 3 wherein the rows of faces are opposed to each other.

5. The cutting accessory of claim 3, wherein the flats are opposed to each other.

6. The cutting accessory of claim 3, wherein the flats lie in planes that are parallel to the longitudinal axis.

7. The cutting accessory of claim 1, wherein the faces are concave.

8. The cutting accessory of claim 1, wherein adjacent faces abut at a crest.

9. The cutting accessory of claim 8, wherein the flat is at a distance from the longitudinal axis that is equal to a distance of the crests from the longitudinal axis.

10. The cutting accessory of claim 1, wherein the shaft further includes a radially extending step that is a transition surface between a distal end of the flat and the outer surface of the shaft located distal to the flat.

11. The cutting accessory of claim 1, wherein the shaft includes a distal section that extends proximally from the tissue working member and the proximal section extends proximally from the distal section, and the distal section has a diameter greater than the diameter of the proximal section.

12. The cutting accessory of claim 1, wherein the tissue working member is one of a bur or a drill bit.

13. The cutting accessory of claim 1, wherein there is a taper at the proximal end of the shaft.

14. The cutting accessory of claim 1, wherein the proximal end of the shaft has a non-circular cross sectional shape.

15. A cutting accessory for use with a powered surgical handpiece, the cutting accessory including:
   an elongated shaft having opposed proximal and distal ends, a longitudinal axis and an outer surface;
   a tissue working member attached to the distal end of the shaft, the tissue working member designed to accomplish a procedure on the living tissue against which the tissue working member is applied; and
   a proximal section that extends proximally from the distal end, the proximal section includes a plurality of faces that extend inwardly from the outer surface of the shaft, each face having at least one shallow portion and shaped to receive a clamping member that holds the shaft to the handpiece, wherein at least two of the faces are arranged linearly so as to extend proximally to distally along the shaft proximal section,
   wherein the shaft includes a flat that extends distally forward of the distalmost face, the flat being located a distance from the shaft longitudinal axis that is greater than the distance shallow portions of the faces are located from the longitudinal axis and less than the distance the outer surface of the shaft is located from the longitudinal axis,
   and wherein the flat has a flat length extending along the axis greater than a face length of any face of the plurality of faces.

16. The cutting accessory of claim 15, wherein adjacent faces abut at a crest.

17. The cutting accessory of claim 16, wherein the flat is at a distance from the longitudinal axis that is equal to a distance of the crests from the longitudinal axis.

18. The cutting accessory of claim 16, wherein the face length is defined between consecutive crests on either side of one face of the plurality of faces.

19. The cutting accessory of claim 15, wherein the shaft further includes a radially extending step that is a transition surface between a distal end of the flat and the outer surface of the shaft located distal to the flat.

20. The cutting accessory of claim 19, wherein the flat length is defined between the radially extending step and the distalmost face of the plurality of faces.

\* \* \* \* \*